United States Patent [19]

Hubele et al.

[11] Patent Number: 4,705,790
[45] Date of Patent: Nov. 10, 1987

[54] N-(2-NITROPHENYL)-4-AMINOPYRIMIDINE MICROBICIDES

[75] Inventors: Adolf Hubele, Magden, Switzerland; Wolfgang Eckhardt, Lörrach, Fed. Rep. of Germany

[73] Assignee: CIBA-GEIGY Corporation, Ardsley, N.Y.

[21] Appl. No.: 780,063

[22] Filed: Sep. 25, 1985

Related U.S. Application Data

[63] Continuation of Ser. No. 594,146, Mar. 28, 1984, abandoned.

[30] Foreign Application Priority Data

Apr. 8, 1983 [CH] Switzerland ................ 1899/83

[51] Int. Cl.$^4$ ................ A61K 31/505; C07D 239/42; C07D 239/46
[52] U.S. Cl. ................ 514/269; 514/274; 544/317; 544/322; 544/331
[58] Field of Search ................ 544/317, 322, 331; 514/269, 274

[56] References Cited

U.S. PATENT DOCUMENTS 3,906,098 9/1975 Barlow et al. ................ 71/92

FOREIGN PATENT DOCUMENTS 0073328 3/1983 European Pat. Off.

OTHER PUBLICATIONS

Journal of Medicinal and Pharmaceutical Chemistry, vol. 5 (1962) pp. 1085–1095, D. E. O'Brien et al.

Primary Examiner—Donald G. Daus
Assistant Examiner—Cecilia Shen
Attorney, Agent, or Firm—Edward McC. Roberts; Meredith C. Findlay

[57] ABSTRACT

The invention relates to novel N-(2-nitrophenyl)-4-aminopyrimidine derivatives of the general formula I

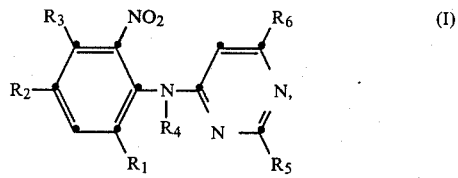

wherein
$R_1$ is $NO_2$ or $CF_3$,
$R_2$ is $NO_2$ or $CF_3$,
$R_3$ is hydrogen or halogen,
$R_4$ is hydrogen or the —C(O)$R_7$ group, wherein $R_7$ is $C_1$–$C_4$alkyl which is unsubstituted or substituted by halogen, $C_1$–$C_3$alkoxy or $C_1$–$C_3$alkylthio,
$R_5$ and $R_6$ are each independently halogen, $C_1$–$C_6$alkoxy, $C_1$–$C_6$alkyl which is substituted by halogen or $C_1$–$C_3$alkoxy, $C_1$–$C_6$alkoxy which is substituted by halogen or $C_1$–$C_3$alkoxy, $C_1$–$C_6$alkylthio or $C_1$–$C_6$alkylthio which is substituted by halogen or $C_1$–$C_3$alkoxy, or are $C_3$–$C_6$cycloalkoxy, $C_3$–$C_6$cycloalkylthio, $C_3$–$C_6$alkenyloxy, $C_3$–$C_6$alkenylthio, $C_3$–$C_6$alkynyloxy, $C_1$–$C_6$alkylsulfoxyl, $C_1$–$C_6$-alkylsulfonyl, $C_1$–$C_6$alkylsulfonyloxy, $C_3$–$C_6$alkenylsulfoxyl, $C_3$–$C_6$alkenylsulfonyl, $C_3$–$C_6$cycloalkylsulfoxyl or $C_3$–$C_6$-cycloalkylsulfonyl.

The invention relates further to methods of preparing these compounds as well as to agrochemical compositions which contain them. Also described is a method of controlling phytopathogenic micro-organisms with the aid of the novel compounds.

16 Claims, No Drawings

N-(2-NITROPHENYL)-4-AMINOPYRIMIDINE MICROBICIDES

This is a continuation of application Ser. No. 594,146 filed on Mar. 28, 1984, now abandoned.

The present invention relates to novel N-(2-nitrophenyl)-4-aminopyrimidine derivatives of the formula I below. The invention further relates to the preparation of these compounds and to microbicidal compositions which contain at least one of these compounds as active ingredient. The invention also relates to the preparation of such microbicidal compositions and to the use of the novel compounds or compositions for controlling harmful microorganisms, preferably phytopathogenic fungi.

Specifically, the present invention relates to compounds of the general formula I

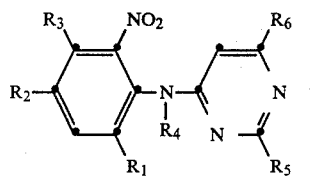

wherein
$R_1$ is $NO_2$ or $CF_3$,
$R_2$ is $NO_2$ or $CF_3$,
$R_3$ is hydrogen or halogen,
$R_4$ is hydrogen or the $-C(O)R_7$ group, wherein $R_7$ is $C_1-C_4$alkyl which is unsubstituted or substituted by halogen, $C_1-C_3$alkoxy or $C_1-C_3$alkylthio,
$R_5$ and $R_6$ are each independently halogen, $C_1-C_6$alkoxy, $C_1{-}C_6$alkyl which is substituted by halogen or $C_1-C_3$alkoxy, $C_1-C_6$alkoxy which is substituted by halogen or $C_1-C_3$alkoxy, $C_1-C_6$alkylthio, $C_1-C_6$alkylthio which is substituted by halogen or $C_1-C_3$alkoxy, or are $C_3-C_6$cycloalkoxy, $C_3-C_6$cycloalkylthio, $C_3-C_6$alkenyloxy, $C_3-C_6$alkenylthio, $C_3-C_6$alkynyloxy, $C_1-C_6$alkylsulfoxyl, $C_1-C_6$alkylsulfonyl, $C_1-C_6$alkylsulfonyloxy, $C_3-C_6$alkenylsulfoxyl, $C_3-C_6$alkenylsulfonyl, $C_3-C_6$cycloalkylsulfoxyl or $C_3-C_6$cycloalkylsulfonyl.

Depending on the number of indicated carbon atoms, alkyl by itself or as moiety of another substituent comprises e.g. the following groups: methyl, ethyl, propyl, butyl, pentyl, hexyl etc. and the isomers thereof, e.g. isopropyl, isobutyl, tert-butyl, isopentyl etc. Alkenyl is e.g. vinyl, propen-1-yl, allyl, buten-1-yl, buten-2-yl, buten-3-yl etc., as well as chains containing several double bonds. Alkynyl is e.g. propyn-1-yl, propargyl, butyn-1-yl, butyn-2-yl etc., with propargyl being preferred. Haloalkyl is in particular a monohalogenated to perhalogenated alkyl substituent, e.g. $CHCl_2$, $CH_2Cl$, $CCl_3$, $CF_3$, $CH_2CH_2Cl$ etc. Throughout this specification, halogen denotes fluorine, chlorine, bromine or iodine, with chlorine, bromine or fluorine being preferred. Cycloalkyl is e.g. cyclopropyl, cyclobutyl, cyclopentyl, cyclohexyl or cycloheptyl, with cyclopropyl and cyclohexyl being preferred.

The compounds of formula I are oils, resins or mainly crystalline solids which are stable under normal conditions and have extremely valuable microbicidal properties. They can be used for example in agriculture or related fields preventively and curatively for controlling phytopathogenic micro-organisms. The compounds of formula I have excellent fungicidal properties when applied in wide ranges of concentration and their use poses no problems.

The following subgroups Ia to Ii are preferred on account of their pronounced microbicidal, especially fungicidal, properties:

Group Ia: compounds of the formula I, wherein $R_1$ is $NO_2$, $R_2$ is $CF_3$, $R_3$ is chlorine and $R_4$ is hydrogen, $R_5$ is halogen, $C_1-C_6$alkoxy, chlorine- or bromine-substituted $C_1-C_3$alkyl, $C_1-C_3$alkoxy-substituted $C_1-C_3$alkoxy, $C_1-C_6$alkylthio, cyclopentyloxy, cyclohexyloxy, cyclopentylthio, cyclohexylthio, $C_3-C_6$alkenyloxy, $C_3-C_6$alkenylthio, $C_3-C_6$alkynyloxy, $C_1-C_3$alkylsulfoxyl, $C_1-C_6$alkylsulfonyl, $C_1-C_3$alkylsulfonyloxy or cyclohexylsulfonyl; and $R_6$ is halogen.

Group Ib: compounds of the formula I, wherein $R_1$ is $NO_2$, $R_2$ is $CF_3$, $R_3$ is chlorine or bromine, $R_5$ is halogen, $C_1-C_4$alkoxy, $C_1-C_3$alkyl which is substituted by chlorine or bromine, $C_1-C_2$alkoxy which is substituted by methoxy, $C_1-C_4$alkylthio, $C_3-C_4$alkenyloxy, $C_3-C_4$alkynyloxy or $C_1-C_3$alkylsulfonyl; and $R_6$ is fluorine, chlorine or bromine.

Particularly preferred compounds of the formula I within this subgroup Ib are those wherein $R_3$ and $R_6$ are chlorine and $R_5$ is fluorine, chlorine, bromine, $C_1-C_3$alkoxy, $C_1-C_3$alkylthio, $OCH_2CH_2OCH_3$, $OCH_2CH=CH_2$ or $OCH_2=CH$ (group Ib').

Group Ic: compounds of the formula I, wherein $R_1$ is $CF_3$, $R_2$ is $NO_2$, $R_3$ is hydrogen and $R_4$ is hydrogen, $R_5$ is halogen, $C_1-C_6$alkoxy, chlorine- or bromine-substituted $C_1-C_3$alkyl, $C_1-C_3$alkoxy-substituted $C_1-C_3$alkoxy, $C_1-C_6$alkylthio, cyclopentyloxy, cyclohexyloxy, cyclopentylthio, cyclohexylthio, $C_3-C_6$alkenyloxy, $C_3-C_6$alkenylthio, $C_3-C_6$alkynyloxy, $C_1-C_3$alkylsulfoxyl, $C_1-C_6$alkylsulfonyl, $C_1-C_3$alkylsulfonyloxy or cyclohexylsulfonyl; and $R_6$ is halogen.

Group Id: compounds of the formula I, wherein $R_1$ is $CF_3$, $R_2$ is $NO_2$, $R_3$ is chlorine or bromine, $R_5$ is halogen, $C_1-C_4$alkoxy, chlorine- or bromine-substituted $C_1-C_3$alkyl, methoxy-substituted $C_1-C_2$alkoxy, $C_1-C_4$alkylthio, $C_3-C_4$alkenyloxy, $C_3-C_4$alkynyloxy or $C_1-C_3$alkylsulfonyl; and $R_6$ is fluorine, chlorine or bromine.

Particularly preferred compounds of the formula I within this subgroup Id are those wherein $R_3$ and $R_6$ are chlorine and $R_5$ is fluorine, chlorine, bromine, $C_1-C_3$alkoxy, $C_1-C_3$alkylthio, $OCH_2CH_2OCH_3$, $OCH_2CH=CH_2$ or $OCH_2C\equiv CH$ (=group Id').

Group Ie: compounds of the formula I, wherein $R_1$ is $NO_2$, $R_2$ is $CF_3$, $R_3$ is halogen and $R_4$ is hydrogen, $R_5$ is $C_1-C_3$alkoxy, $C_1-C_3$alkylthio, $C_1-C_3$alkylsulfoxyl or $C_1-C_3$alkylsulfonyl; and $R_6$ is halogen.

Group If: compounds of the formula I, wherein $R_1$ is $NO_2$, $R_2$ is $CF_3$, $R_3$ is chlorine and $R_4$ is hydrogen, and each of $R_5$ and $R_6$ independently is halogen, $C_1-C_6$alkoxy, chlorine- or bromine-substituted $C_1-C_3$alkyl, $C_1-C_3$alkoxy-substituted $C_1-C_3$alkoxy, $C_1-C_6$alkylthio, cyclopentyloxy, cyclohexyloxy, cyclopentylthio, cyclohexylthio, $C_3-C_6$alkenyloxy, $C_3$alkenylthio, $C_3-C_6$alkynyloxy, $C_1-C_3$alkylsulfoxyl, $C_1-C_6$alkylsulfonyl, $C_1-C_3$alkylsulfonyloxy or cyclohexylsulfonyl.

Group Ig: compounds of the formula I, wherein $R_1$ is $CF_3$, $R_2$ is $NO_2$, $R_3$ is hydrogen and $R_4$ is hydrogen, and each of $R_5$ and $R_6$ independently is $C_1-C_3$alkoxy, $C_1-C_3$alkylthio, $C_3$alkenyloxy, $C_1-C_3$alkenylsulfoxyl or $C_1-C_3$alkenylsulfonyl.

Group Ih: compounds of formula I, wherein $R_1$ is $CF_3$ or $NO_2$, $R_2$ is $CF_3$ or $NO_2$, $R_3$ is hydrogen or chlorine, $R_4$ is the $C(O)-R_7$ group, wherein $R_7$ is $C_1-C_3$alkyl, halogen-substituted $C_1$–$C_3$alkyl or $C_1$–$C_3$-alkoxy-substituted $C_1$–$C_3$alkyl; $R_5$ is halogen, $C_1$–$C_3$alkoxy or $C_1$–$C_3$alkylthio, and $R_6$ is chlorine. $C_1$–$C_3$alkylthio and $R_6$ is chlorine.

Group Ii: compounds of the formula I, wherein $R_1$ is $NO_2$, $R_2$ is $CF_3$, $R_3$ is hydrogen and $R_4$ is hydrogen, $R_5$ is halogen, $C_1$–$C_6$alkoxy, chlorine- or bromine-substituted $C_1$–$C_3$alkyl, $C_1$–$C_3$alkoxy-substituted $C_1$–$C_3$alkoxy, $C_1$–$C_6$alkylthio, cyclopentyloxy, cyclohexyloxy, cyclopentylthio, cyclohexylthio, $C_3$–$C_6$alkenyloxy, $C_3$–$C_6$alkenylthio, $C_3$–$C_6$alkynyloxy, $C_1$–$C_3$alkylsulfoxy, $C_1$–$C_6$alkylsulfonyl, $C_1$–$C_3$alkylsulfonyloxy or cyclohexylsulfonyl; and $R_6$ is halogen.

Examples of particularly preferred compounds are:

N-(3'-chloro-2',6'-dinitro-4'-trifluoromethylphenyl)-4-amino-2,6-dichloropyrimidine; (compound 1.1)

N-(2',4'-dinitro-6'-trifluoromethylphenyl)-4-amino-2,6-dichloropyrimidine; (compound 2.1)

N-(3α-chloro-2',6'-dinitro-4'-trifluoromethylphenyl)-4-amino-6-chloro-2-methylmercatpopyrimidine; (compound 1.5)

N-(2',6'-dinitro-4'-trifluoromethylphenyl)-4-amino-6-chloro-2-methyl-mercaptopyrimidine; (compound 7.32)

N-(3'-chloro-2',6'-dinitro-4'-trifluoromethylphenyl)-4-amino-6-chloro-2-methoxypyrimidine; (compound 1.4)

N-(3'-chloro-2',6'-dinitro-4'-trifluoromethylphenyl)-4-amino-6-chloro-2-ethoxypyrimidine; (compound 1.12)

N-(3'-chloro-2',6'-dinitro-4'-trifluoromethylphenyl)-4-amino-6-chloro-2-ethylmercatpopyrmidine; (compound 1.63)

N-(3'-chloro-2',6'-dinitro-4'-trifluoromethylphenyl)-4-amino-6-chloro-2-sec-butylmercaptopyrimidine; (compound 1.80)

N-(2',6'-dinitro-4'-trifluoromethylphenyl)-4-amino-2,6-dichloropyrimidine; (compound 7.1)

N-(2',4'-dinitro-6'-trifluoromethylphenyl)-4-amino-2-methoxy-6-chloropyrmidine; (compound 2.7)

N-(2',4'-dinitro-6'-nitrofluoromethylphenyl)-4-amino-2-ethoxy-6-chloropyrimidine; (compound 2.6).

The compounds of formula I are prepared by reacting a compound of the formula II

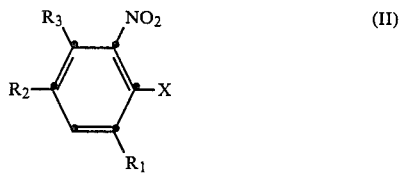

with a pyrimidine derivative of the formula III

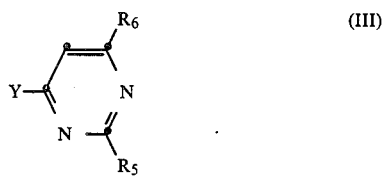

in the presence of a base, to give a compound of the formula I'

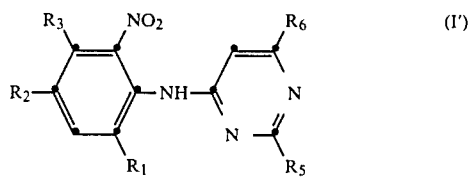

and, to obtain an N-acylated derivative, N-acylating the compound of the formula I' with a reactive derivative of the carboxylic acid of the formula IV $$R_7COOH \qquad (IV)$$

in which formulae above the substituents $R_1$ to $R_7$ are as defined for formula I and X and Y are $NH_2$ or halogen, with the proviso that, if X is halogen, Y is $NH_2$ and, if X is $NH_2$, Y is halogen.

The following reaction conditions are advantageous for the preparation of the compounds of formula I and/or I':

The N-alkylation of (II) with (III) to give (I') and the N-acylation of (I') with (IV) to give (I) take place with dehydrohalogenation. The reaction temperature of the N-alkylation is in the range from −20° to +150° C., preferably from −20° to +30° C., and that for the N-acylation is in the range from 0° to 180° C., preferably from 0° to +150° C. or at the boiling point of the solvent or solvent mixture. In both reactions it is convenient to use an acid acceptor or a condensing agent. Examples of suitable acid acceptors or condensing agents are organic and inorganic bases, e.g. tertiary amines such as trialkylamines (trimethylamine, triethylamine, tripropylamine etc.), pyridine and pyridine bases (4-dimethylaminopyridine, 4-pyrrolidylaminopyridine etc.), oxides, hydroxides, carbonates and bicarbonates of alkali metals and alkaline earth metals, as well as alkali metal acetates.

The reactions may be conducted in the presence of inert solvents or diluents. Examples of suitable solvents and diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxan, tetrahydrofuran; nitriles such as acetonitrile and propionitrile; N,N-dialkylated amides such as dimethylformamide; dimethylsulfoxide; ketones such as acetone, diethyl ketone, methyl ethyl ketone; and mixtures of such solvents.

The reaction of (II) with (III) can also be carried out in an aqueous two-phase system in accordance with the generally known principle of phase transfer catalysis.

The following solvents for example are suitable for the organic water-immiscible phase: aliphatic and aromatic hydrocarbons such as pentane, hexane, cyclohexane, petroleum ether, ligroin, benzene, toluene, xylenes etc.; halogenated hydrocarbons such as dichloromethane, chloroform, carbon tetrachloride, ethylene dichloride, 1,2-dichloroethane, tetrachloroethylene and the like, or aliphatic ethers such as diethyl ether, diisopropyl ether, tert-butylmethyl ether etc. Examples of suitable phases transfer catalysts are: tetraalkylammonium halides, hydrogen sulfates or hydroxides, e.g. tetrabutylammonium chloride, tetrabutylammonium bromide, tetrabutylammonium iodide, triethylbenzylammonium chloride or triethylbenzylammonium bromide, tetrapropylammonium chloride, tetrapropyl ammonium bromide or tetrapropylammonium iodide etc. Suitable phase transfer catalysts are also phosphonium salts. The reaction temperatures are generally in the range from −30° to 130° C. or may also be at the boiling point of the solvent or mixture of solvents.

Unless otherwise expressly specified, one or more inert solvents or diluents may be present in the preparation of all starting materials, intermediates and final products mentioned herein. Examples of suitable inert solvents or diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxane, tetrahydrofurane; nitriles such as acetonitrile, propionitrile; N,N-dialkylated amides such as dimethyl formamide; dimethylsulfoxide; ketones such as acetone, diethyl ketone, methyl ethyl ketone; and mixtures of such solvents with each other. It can often be convenient to carry out the reaction, or partial steps of a reaction, under an inert gas atmosphere and/or in absolute solvents. Suitable inert gases are nitrogen, helium, argon or, in certain cases, also carbon dioxide.

The above described preparatory process, including all partial steps, constitutes an important object of the present invention.

Surprisingly, it has been found that the compounds of formula I have for practical purposes a very useful microbicidal spectrum against phytopathogenic fungi and bacteria. They have very advantageous curative, systemic and, in particular, preventive properties, and can be used for protecting numerous cultivated plants. With the compounds of formula I it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms.

The compounds of formula I are effective against the phytopathogenic fungi belonging to the following classes: Fungi imperfecti (e.g. Botrytis, Helminthosporium, Fusarium, Septoria, Cercospora and Alternaria); Basidiomycetes (e.g. of the genera Hemileia, Rhizocotonia, Puccinia); and, in particular, against the class of the Ascomycetes (e.g. Venturia, Podosphaera, Erysiphe, Monilinia, Uncinula). In addition, the compounds of formula I have a systemic action. They can also be used as seed dressing agents for protecting seeds (fruit, tubers, grains) and plant cuttings against fungus infections as well as against phytopathogenic microorganisms which occur in the soil.

Accordingly, the invention also relates to microbicidal compositions and to the use of compounds of the formula I for controlling phytophatogenic microorganisms, especially harmful fungi, and for the preventive treatment of plants to protect them from attack by such microorganisms.

The invention further embraces the preparation of agrochemical compositions which comprises homogeneously mixing the active ingredient with one or more compounds or groups of compounds described herein. The invention furthermore relates to a method of treating plants, which comprises applying thereto the compounds of the formula I or the novel compositions.

Target crops to be protected within the scope of the present invention comprise e.g. the following species of plants: cereals (wheat, barley, rye, oats, rice, sorghum and related crops), beet (sugar beet and fodder beet), drupes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

The compounds of formula I are normally applied in agriculture the form of compositions and can be applied to the crop area or plant to be treated, simultaneously or in succession, with further compounds. These compounds can be both fertilisers or micronutrient donors or other preparations that influence plant growth. They can also be selective herbicides, fungicides, bactericides, nematicides, mollusicides or mixtures of several of these preparations, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers.

A preferred method of applying a compound of the formula I or an agrochemical composition which contains at least one of said compounds, is foliar application. The number of applications and the rate of application depend on the risk of infestation by the corresponding pathogen (type of fungus). However, the compound of formula I can also penetrate the plant through the roots via the soil (systemic action) by impregnating the locus of the plant with a liquid composition, or by applying the compounds in solid form to the soil, e.g. in granular form (soil application). The compounds of formula I may also be applied to seeds (coating) by impregnating the seeds either with a liquid formulation containing a compound of the formula I, or coating them with a solid formulation. In special cases, further types of application are also possible, e.g. selective treatment of the plant stems or buds.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl choline, sphingomyeline, phosphatidyl inisotol, phosphatidyl glycerol, lysolecithin, plasmalogenes or cardiolipin, which can be obtained e.g. from animal or plant cells, in particular from the brain, heart, liver, egg yokes or soya beans. Examples of useful physical forms are phosphatidyl choline mixtures. Examples of synthetic phospholipids are dioctanoylphosphatidyl choline and dipalmitoylphosphatidyl choline.

Depending on the nature of the compound of the formula I to be formulated, suitable surface-active compounds are nonionic, cationic and/or anionic sufactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$ alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$ alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1981, "Encyclopedia of Surface Active Agents", Chemical Publishing Co., Inc. New York, 1980.

The agrochemical compositions usually contain 0.1 to 99%, preferably 0.1 to 95%, of a compound of the formula I, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients such as stabilisers, antifoams, viscosity regulators, binders, tackifiers as well as fertilisers or other active ingredients in order to obtain special effects.

Such agrochemical compositions also constitute an object of the present invention.

The invention is illustrated in more detail by the following Examples, without implying any restriction to what is described therein. Parts and percentages are by weight.

PREPARATORY EXAMPLES

Example P1

Preparation of

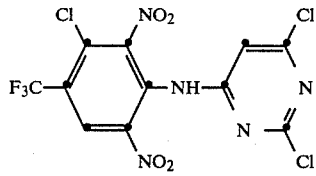 (1.1)

N-(3'-Chloro-2',6'-dinitro-4'-trifluoromethylphenyl)-4-amino-2,6-chloropyrimidine With stirring, 16.5 parts of 85% powdered potassium hydroxide are added, in portions, at room temperature to a solution of 19.1 parts of 2,6-dichloro-4-aminopyrimidine in 430 ml of tetrahydrofuran. During this addition, the temperature rises to about 24° C. in the course of half an hour. The reaction mixture is cooled to 0° C. and 35.4 parts of 2,4-dichloro-3,5-dinitrobenzotrifluoride in 120 ml of tetrahydrofuran are added dropwise to the beige-coloured suspension, which turns red. The reaction mixture is stirred for 14 hours at room temperature, poured into ice-water, acidified with 15 ml of concentrated hydrochloric acid, and extracted with two 300 ml portions of ethyl acetate. The combined extracts are washed with two 100 ml portions of water, dried over sodium sulfate, filtered and dried. The oily residue is crystallised from petroleum ether. The crystals are isolated by filtration and recrystallised from chloroform. The beige-coloured crystals so obtained have a melting point of 174°–177° C.

EXAMPLE P2

Preparation of

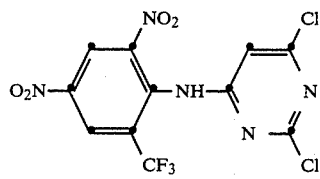 (2.1)

N-(2',4'-Dinitro-6'-trifluoromethylphenyl)-4-amino-2,6-dichloropyrimidine 7.24 parts of 85% powdered potassium hydroxide are added to a solution of 8.2 parts of 2,6-dichloro-4-aminopyrimidine in 200 ml of absolute tetrahydrofuran. The mixture is cooled to 0° C. and then 13.5 parts of 2-chloro-3,5-dinitrobenzotrifluoride in 100 ml of absolute tetrahydrofuran are added in portions, with stirring, over half an hour. During this addition, the colour of the reaction solution turns from yellow to red. The reaction mixture is stirred for 12 hours and then poured into 500 ml of ice-water, acidified with 8 ml of hydrochloric acid, and extracted with two 200 ml portions of ethyl acetate. The combined extracts are washed with 50 ml of water, dried over sodium sulfate, filtered and concentrated. The crude product is crystallised from methanol. Melting point: 198°–200° C.

Example P3

Preparation of

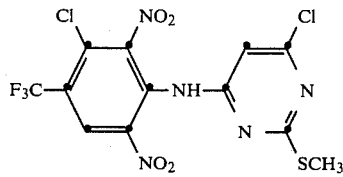 (1.5)

N-(3'-Chloro-2',6'-dinitro-4'-trifluoromethylphenyl)-4-amino-6-chloro-2-methylmercaptopyrimidine 7.9 parts of finely powdered 85% potassium hydroxide are dissolved in 70 ml of dimethylsulfoxide. To this solution is added dropwise a solution of 17.6 parts of 4-amino-6-chloro-2-methylmercaptopyrimidine in 80 ml of dimethylsulfoxide at about 15° C., and the reaction mixture is subsequently stirred for half an hour at room temperature. Then 30.5 parts of 1,3-dichloro-2,6-dinitro-4-trifluoromethylbenzene in 100 ml of dimethylsulfoxide are added dropwise at about 115° C. The reaction mixture is stirred overnight at room temperature, then poured into 2 liters of ice-water and extracted with ethyl acetate. The combined extracts are washed repeatedly with water, dried over sodium sulfate, filtered and concentrated. The crude product is purified by column chromatography over silica gel with dichloromethane as eluant. Yield: 22.3 parts of the title compound with a melting point of 171°–175° C.

The following compounds of formula I are prepared in corresponding manner:

TABLE 1

Compounds of the formula

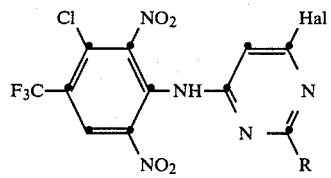

| Compound | R | Hal | Physical data [°C.] |
|---|---|---|---|
| 1.1 | Cl | Cl | m.p. 174–177 |
| 1.2 | OCH$_3$ | F | resin |
| 1.3 | Br | Br | resin |
| 1.4 | OCH$_3$ | Cl | m.p. 199–201 |
| 1.5 | SCH$_3$ | Cl | m.p. 171–175 |
| 1.6 | O—C(CH$_3$)(C$_2$H$_5$)—C≡CH | Cl | |
| 1.7 | OC$_2$H$_5$ | F | resin |
| 1.8 | OCH$_2$CH$_2$OCH$_3$ | Cl | m.p. 128–130 |
| 1.9 | F | F | resin |
| 1.10 | OC$_3$H$_7$—i | F | |
| 1.11 | OCH$_2$CH=CHCH$_3$ | Cl | |
| 1.12 | OC$_2$H$_5$ | Cl | m.p. 164–169 |
| 1.13 | OCH$_2$CH(C$_2$H$_5$)$_2$ | F | |
| 1.14 | OCH$_2$CH=CH$_2$ | Cl | semicristalline |
| 1.15 | OC$_3$H$_7$—n | Cl | m.p. 165–166 |
| 1.16 | OCH$_2$CH$_2$OC$_2$H$_5$ | Cl | |
| 1.17 | J | I | |
| 1.18 | SCH$_3$ | F | |
| 1.19 | OC$_3$H$_7$—i | Cl | |
| 1.20 | OCH$_2$C≡CH | Cl | semicristalline |
| 1.21 | SC$_2$H$_5$ | F | |
| 1.22 | OC$_4$H$_9$—n | Cl | |
| 1.23 | SCH$_2$CH=CH$_2$ | Cl | |
| 1.24 | OC(CH$_3$)$_2$C≡CH | Cl | |

TABLE 1-continued

Compounds of the formula

[Structure: benzene ring with Cl, NO₂, F₃C, NO₂ substituents, NH linked to pyrimidine ring with Hal and R]

| Compound | R | Hal | Physical data [°C.] |
|---|---|---|---|
| 1.25 | SC₃H₇—i | F | |
| 1.26 | O(CH₂)₆Cl | Cl | |
| 1.27 | OCH(CH₃)C₂H₅ | Cl | semicristalline |
| 1.28 | OCH(CH₃)C≡CH | Cl | |
| 1.29 | O—cyclohexyl | Cl | |
| 1.30 | O—C₄H₉—t | Cl | |
| 1.31 | S—C₄H₉—t | F | |
| 1.32 | O(CH₂)₃Cl | Cl | resin |
| 1.33 | S(O)C₂H₅ | Cl | |
| 1.34 | OCH₂CH₂Cl | F | |
| 1.35 | S—cyclohexyl | Cl | |
| 1.36 | S(O)CH₃ | Cl | |
| 1.37 | OCH₂CF₃ | Cl | semicristalline |
| 1.38 | OCH₂CH₂OCH₃ | F | |
| 1.39 | OC₅H₁₁—n | Cl | |
| 1.40 | S(O)₂C₂H₅ | Cl | |
| 1.41 | OCH₂CCl₃ | Cl | |
| 1.42 | S(O)₂CH₃ | Cl | decomp. from 102 |
| 1.43 | OCH₂CH=CH₂ | F | |
| 1.44 | OCH₂—CH(CH₃)C₂H₅ | Cl | |
| 1.45 | OCH₂CH(Br)CH₂Br | Cl | |
| 1.46 | OC(CH₃)₂C₂H₅ | Cl | |
| 1.47 | S(O)₂C₃H₇—n | Cl | |
| 1.48 | OCH(CH₃)CH₂CH₂CH₃ | Cl | |
| 1.49 | OCH₃ | Br | resin |
| 1.50 | OC₂H₅ | I | |
| 1.51 | OCH₂—C≡CH | F | |
| 1.52 | OC₆H₁₃—n | Cl | |
| 1.53 | OCH₂CH₂Br | Cl | semicristalline |
| 1.54 | OCH₂CH(C₂H₅)₂ | Cl | |
| 1.55 | SCH₃ | Br | |
| 1.56 | S(O)₂CH₃ | F | |
| 1.57 | OC₂H₅ | Br | resin |
| 1.58 | OCH₂CH(CH₃)CH₂CH₃ | Cl | |
| 1.59 | S(O)₂CH₃ | Br | |
| 1.60 | OCH₃ | I | |
| 1.61 | S(O)₂C₂H₅ | F | |
| 1.62 | OC(CH₃)C₂H₅)C₂H₅ | Cl | |
| 1.63 | SC₂H₅ | Cl | m.p. 175-176 |
| 1.64 | SC₅H₁₁—n | Cl | |
| 1.65 | S(O)₂C₄H₉—n | Cl | |
| 1.66 | OCH(CH₃)CH₂CH(CH₃)₂ | Cl | |
| 1.67 | S(O)₃C₃H₇—i | F | |
| 1.68 | SC₃H₇—n | Cl | |
| 1.69 | SC₆H₁₃—n | Cl | |
| 1.70 | OCH₂CH₂Cl | Cl | |
| 1.71 | SCH₃ | I | |
| 1.72 | S(O)₂CH₃ | I | |
| 1.73 | SC₃H₇—i | Cl | |
| 1.74 | SC₂H₅ | Br | resin |
| 1.75 | S(O)₂C₆H₁₃—n | Cl | |
| 1.76 | OC₃H₇—i | I | |
| 1.77 | SC₄H₉—n | Cl | |
| 1.78 | SC₃H₇—n | I | |
| 1.79 | S(O)₂C₂H₅ | Br | |
| 1.80 | SCH(CH₃)C₂H₅ | Cl | m.p. 152-155 |
| 1.81 | OCH₂C≡CH | I | |
| 1.82 | SC₄H₉—t | Cl | |
| 1.83 | S(O)₂cyclohexyl | Cl | |
| 1.84 | OCH₂CH(CH₃)₂ | Cl | m.p. 174-177 |

TABLE 2

Compounds of the formula

[Structure: benzene ring with NO₂, O₂N, CF₃ substituents, NH linked to pyrimidine ring with Hal and R]

| Compound | R | Hal | Physical data [°C.] |
|---|---|---|---|
| 2.1 | Cl | Cl | m.p. 198-200 |
| 2.2 | OCH₃ | F | resin |
| 2.3 | OC₃H₇—i | Cl | resin |
| 2.4 | S(O)₂CH₃ | Cl | |
| 2.5 | F | F | resin |
| 2.6 | OC₂H₅ | Cl | m.p. 150-152 |
| 2.7 | OCH₃ | Cl | m.p. 170-172 |
| 2.8 | OC₂H₅ | F | resin |
| 2.9 | S(O)₂C₂H₅ | Cl | |
| 2.10 | OC₃H₇—n | Cl | m.p. 76-78 |
| 2.11 | S(O)CH₃ | Cl | |
| 2.12 | Br | Br | resin |
| 2.13 | OC₄H₉—n | Cl | |
| 2.14 | S—cyclohexyl | Cl | |
| 2.15 | I | I | |
| 2.16 | OC₃H₇—i | F | |
| 2.17 | OC₄H₉—t | Cl | |
| 2.18 | S(O)C₂H₅ | Cl | |
| 2.19 | SCH₃ | F | |
| 2.20 | S(O)₂C₃H₇—n | Cl | |
| 2.21 | OCH₂CH(CH₃)C₂H₅ | Cl | |
| 2.22 | OCH(CH₃)C₂H₅ | Cl | semicristalline |
| 2.23 | OC₅H₁₁—n | Cl | |
| 2.24 | O—cyclohexyl | Cl | |
| 2.25 | SC₂H₅ | F | |
| 2.26 | OC₆H₁₃—n | Cl | |
| 2.27 | OCH₃ | Br | resin |
| 2.28 | OC₆C₁₃—n | F | |
| 2.29 | SC₄H₉—t | F | |
| 2.30 | OC₂H₅ | Br | resin |
| 2.31 | OCH₂CH(CH₃)CH₂CH₃ | Cl | |
| 2.32 | SCH₃ | Cl | m.p. 182-188 |
| 2.33 | OC₃H₇—i | Br | |
| 2.34 | OCH₂CH(C₂H₅)₂ | Cl | |
| 2.35 | OCH₂CH₂OCH₃ | F | |
| 2.36 | SCH₃ | Br | |
| 2.37 | OC(CH₃)₂C≡CH | Cl | |
| 2.38 | S(O)₂CH₃ | F | |
| 2.39 | SC₄H₉—n | Cl | |
| 2.40 | SC₂H₅ | Cl | m.p. 90-93 |
| 2.41 | SCH₂CH=CH₂ | Cl | |
| 2.42 | OCH₂CF₃ | Cl | semicristalline |
| 2.43 | S(O)₂C₂H₅ | F | |
| 2.44 | SC₂H₅ | Br | resin |
| 2.45 | SC₃H₇—n | Cl | |
| 2.46 | SC₃H₇—i | Br | |
| 2.47 | SC₃H₇—i | Cl | |
| 2.48 | OC(CH₃)₂C≡CH | Cl | |
| 2.49 | OCH₂C≡CH | Cl | semicristalline |
| 2.50 | OCH₂CH₂Br | Br | |
| 2.51 | S(O)₂CH₃ | Br | |
| 2.52 | S(O)₂C₆H₁₃—n | F | |
| 2.53 | SC₄H₉—n | Cl | |
| 2.54 | SO₂C₂H₅ | Br | |
| 2.55 | OCH₂CH=CH₂ | Cl | semicristalline |
| 2.56 | OCH₃ | I | |
| 2.57 | SC₄H₉—t | Cl | |
| 2.58 | OC₂H₅ | I | |
| 2.59 | SC₆H₁₃—n | Cl | |
| 2.60 | OCH₂CH₂OC₂H₅ | Cl | |
| 2.61 | OCH₂CH(CH₃)₂ | Cl | m.p. 144-145 |
| 2.62 | SCH₃ | I | |
| 2.63 | OCH₂CH₂Cl | Cl | |
| 2.64 | S(O)₂CH₃ | I | |
| 2.65 | S(O)₂C₂H₅ | I | |
| 2.66 | O(CH₂)₃Cl | Cl | resin |
| 2.67 | SC₂H₅ | I | |
| 2.68 | OCH₂CH=CH₂ | I | |

TABLE 2-continued

Compounds of the formula

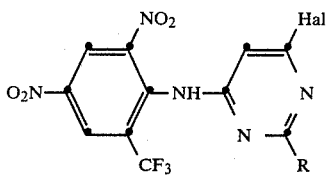

| Compound | R | Hal | Physical data [°C.] |
|---|---|---|---|
| 2.69 | OCH$_2$CH$_2$OCH$_3$ | Cl | m.p. 160-162 |
| 2.70 | OCH$_2$C≡CH | I | |

TABLE 3

Compounds of the formula

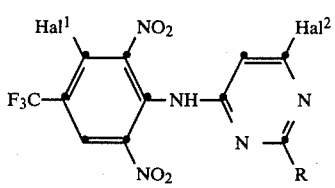

| Compound | Hal$^1$ | Hal$^2$ | R | Physical data [°C.] |
|---|---|---|---|---|
| 3.1 | Br | Cl | OCH$_3$ | |
| 3.2 | F | Br | OCH$_3$ | |
| 3.3 | F | I | OCH$_3$ | |
| 3.4 | F | Cl | OCH$_3$ | |
| 3.5 | Br | Cl | SCH$_3$ | |
| 3.6 | F | Br | SCH$_3$ | |
| 3.7 | F | Cl | SCH$_3$ | |
| 3.8 | F | Br | S(O)$_2$CH$_3$ | |
| 3.9 | Br | Cl | S(O)$_2$CH$_3$ | |
| 3.10 | Br | Cl | SC$_3$H$_7$—i | |
| 3.11 | F | Cl | S(O)$_2$CH$_3$ | |
| 3.12 | F | F | SCH$_3$ | |
| 3.13 | I | Cl | OCH$_3$ | |
| 3.14 | Br | Br | OCH$_3$ | |
| 3.15 | Br | F | OCH$_3$ | |
| 3.16 | I | Cl | SCH$_3$ | |
| 3.17 | Br | F | SCH$_3$ | |
| 3.18 | Br | Br | SCH$_3$ | |
| 3.19 | I | Cl | S(O)$_2$CH$_3$ | |
| 3.20 | I | Cl | SC$_2$H$_5$ | |
| 3.21 | Br | I | OCH$_3$ | |
| 3.22 | I | Cl | OC$_3$H | |
| 3.23 | I | Cl | OC$_2$H$_5$ | |

TABLE 4

Compounds of the formula

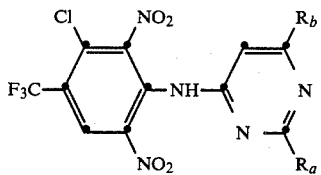

| Compound | R$_a$ | R$_b$ | Physical data [°C.] |
|---|---|---|---|
| 4.1 | OCH$_3$ | SCH$_3$ | |
| 4.2 | SC$_3$H$_7$—i | OCH$_3$ | |
| 4.3 | S(O)$_2$CH$_3$ | OCH$_3$ | |
| 4.4 | OCH$_3$ | OCH$_3$ | m. p. 136-140 |
| 4.5 | SC$_3$H$_7$—i | OC$_2$H$_5$ | |
| 4.6 | S(O)$_2$CH$_3$ | OC$_2$H$_5$ | |
| 4.7 | OCH$_3$ | OC$_2$H$_5$ | |

TABLE 4-continued

Compounds of the formula

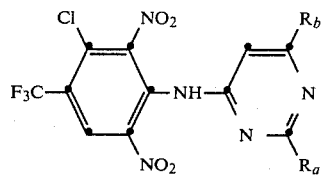

| Compound | R$_a$ | R$_b$ | Physical data [°C.] |
|---|---|---|---|
| 4.8 | S(O)$_2$CH$_3$ | OC$_3$H$_7$—i | |
| 4.9 | OCH$_3$ | SC$_2$H$_5$ | |
| 4.10 | SC$_3$H$_7$—i | SCH$_3$ | |
| 4.11 | S(O)$_2$CH$_3$ | SCH$_3$ | |
| 4.12 | OCH$_3$ | SC$_3$H$_7$—i | |
| 4.13 | S(O)$_2$CH$_3$ | SC$_2$H$_5$ | |
| 4.14 | SC$_3$H$_7$—i | SC$_2$H$_5$ | |
| 4.15 | S(O)$_2$CH$_3$ | SC$_4$H$_9$—t | |
| 4.16 | OCH$_3$ | SC$_4$H$_9$—t | |
| 4.17 | S(O)$_2$CH$_3$ | S(O)$_2$CH$_3$ | |
| 4.18 | SC$_3$H$_7$—i | SC$_3$H$_7$—i | |
| 4.19 | S(O)$_2$CH$_3$ | OCH$_2$CH=CH$_2$ | |
| 4.20 | OCH$_3$ | OCH$_2$CH=CH$_2$ | |
| 4.21 | SO$_2$CH$_3$ | OCH$_2$CH=CHCH$_3$ | |
| 4.22 | SC$_3$H$_7$—i | SC$_4$H$_9$—t | |
| 4.23 | OCH$_3$ | OCH$_2$CH$_2$Cl | |
| 4.24 | OCH$_3$ | S(O)$_2$CH$_3$ | |
| 4.25 | S(O)$_2$CH$_3$ | S(O)$_2$C$_2$H$_5$ | |
| 4.26 | SC$_3$H$_7$—i | OCH$_2$CH=CH$_2$ | |
| 4.27 | OCH$_3$ | S(O)$_2$C$_2$H$_5$ | |
| 4.28 | S(O)$_2$C$_2$H$_5$ | S(O)$_2$CH$_3$ | |
| 4.29 | S(O)$_2$C$_2$H$_5$ | OCH$_3$ | |
| 4.30 | OC$_2$H$_5$ | OCH$_3$ | |
| 4.31 | S(O)$_2$C$_2$H$_5$ | S(O)$_2$C$_2$H$_5$ | |
| 4.32 | SC$_3$H$_7$—i | OCH$_2$CH$_2$Cl | |
| 4.33 | OC$_2$H$_5$ | OC$_2$H$_5$ | |
| 4.34 | SC$_4$H$_9$—t | OCH$_3$ | |
| 4.35 | OC$_2$H$_5$ | SC$_2$H$_5$ | |
| 4.36 | SC$_4$H$_9$—t | OC$_2$H$_5$ | |
| 4.37 | S(O)$_2$C$_2$H$_5$ | OC$_2$H$_5$ | |
| 4.38 | OC$_2$H$_5$ | SC$_3$H$_7$—i | |
| 4.39 | S(O)$_2$C$_2$H$_5$ | SCH$_3$ | |
| 4.40 | SC$_4$H$_9$—t | SCH$_3$ | |
| 4.41 | OC$_2$H$_5$ | SC$_4$H$_9$—t | |
| 4.42 | S(O)$_2$C$_2$H$_5$ | SC$_2$H$_5$ | |
| 4.43 | SC$_4$H$_9$—t | SC$_2$H$_5$ | |
| 4.44 | OC$_2$H$_5$ | OCH$_2$CH=CH$_2$ | |
| 4.45 | S(O)$_2$C$_2$H$_5$ | SC$_3$H$_7$—i | |
| 4.46 | OC$_2$H$_5$ | OCH$_2$CH$_2$Cl | |
| 4.47 | OC$_2$H$_5$ | SCH$_3$ | |
| 4.48 | S(O)$_2$C$_2$H$_5$ | SC$_4$H$_9$—t | |
| 4.49 | OC$_2$H$_5$ | S(O)$_2$CH$_3$ | |
| 4.50 | SC$_4$H$_9$—t | SC$_3$H$_7$—i | |
| 4.51 | S(O)$_2$C$_2$H$_5$ | OCH$_2$CH=CH$_2$ | |
| 4.52 | OCH$_2$CH=CH$_2$ | OCH$_3$ | |
| 4.53 | OC$_2$H$_5$ | S(O)$_2$C$_2$H$_5$ | |
| 4.54 | S(O)$_2$C$_2$H$_5$ | OCH$_2$CH$_2$Cl | |
| 4.55 | SCH$_3$ | OCH$_3$ | m. p. 70-74 |
| 4.56 | SC$_4$H$_9$—t | SC$_4$H$_9$—t | |
| 4.57 | OCH$_2$CH=CH$_2$ | OC$_2$H$_5$ | |
| 4.58 | SCH$_3$ | OC$_2$H$_5$ | |
| 4.59 | SC$_2$H$_5$ | SC$_2$H$_5$ | |
| 4.60 | SCH$_3$ | SCH$_3$ | |
| 4.61 | OCH$_2$CH=CH$_2$ | SCH$_3$ | |
| 4.62 | SCH$_3$ | SC$_2$H$_5$ | |
| 4.63 | SC$_2$H$_5$ | SC$_3$H$_7$—i | |
| 4.64 | OCH$_2$CH=CH$_2$ | SC$_2$H$_5$ | |
| 4.65 | SCH$_3$ | C$_3$H$_7$—i | |
| 4.66 | SC$_2$H$_5$ | SC$_4$H$_9$—t | |
| 4.67 | SCH$_3$ | SC$_4$H$_9$—t | |
| 4.68 | OCH$_2$CH=CH$_2$ | SC$_2$H$_7$—i | |
| 4.69 | OCH$_2$CH=CH$_2$ | OCH$_2$CH=CH$_2$ | |
| 4.70 | SCH$_3$ | OCH$_2$CH=CH$_2$ | |
| 4.71 | SC$_2$H$_5$ | OCH$_2$CH=CH$_2$ | |
| 4.72 | SCH$_3$ | OCH$_2$CH$_2$Cl | |
| 4.73 | SC$_2$H$_5$ | OCH$_2$CH$_2$Cl | |
| 4.74 | OCH(CH$_3$)CH$_2$CH$_2$CH$_3$ | SCH$_3$ | |

TABLE 4-continued

Compounds of the formula

Cl, NO₂ on benzene ring; F₃C on benzene; NH–C(=N–...)–C(R_b)=... with pyrimidine, R_a

| Compound | R_a | R_b | Physical data [°C.] |
|---|---|---|---|
| 4.75 | SC₂H₅ | OC₂H₅ | |
| 4.78 | SCH₃ | OCH₂CH₂OCH₃ | |
| 4.79 | SC₂H₅ | OCH₂CH₂OCH₃ | |
| 4.80 | SC₂H₅ | OCH₂CH₂OCH₃ | |
| 4.81 | SCH₃ | OCH₂CH₂OC₂H₅ | |
| 4.82 | SC₂H₅ | SCH₃ | |
| 4.83 | SC₂H₅ | OCH₂CH₂OC₂H₅ | |
| 4.84 | SCH₂CH=CH₂ | OCH₃ | resin |

TABLE 5

Compound of the formula

O₂N, NO₂, CF₃ on benzene; NH linker to pyrimidine with R_a, R_b

| Compound | R_a | R_b | Physical data [°C.] |
|---|---|---|---|
| 5.1 | OCH₃ | OCH₃ | |
| 5.2 | SCH₃ | OCH₃ | |
| 5.3 | OCH₃ | OC₂H₅ | |
| 5.4 | SCH₃ | OC₂H₅ | |
| 5.5 | OCH₃ | SCH₃ | |
| 5.6 | SCH₃ | SCH₃ | |
| 5.7 | OCH₃ | SC₂H₅ | |
| 5.8 | SCH₃ | SC₂H₅ | |
| 5.9 | OCH₃ | OC₃H₇—i | |
| 5.10 | SCH₃ | OCH₂CH=CH₂ | |
| 5.11 | OCH₃ | S(O)₂CH₃ | |
| 5.12 | SC₂H₅ | OCH₃ | |
| 5.13 | SC₃H₇—i | OCH₃ | |
| 5.14 | OCH₃ | S(O)₂C₂H₅ | |
| 5.15 | SC₂H₅ | OC₂H₅ | |
| 5.16 | SC₃H₇—i | OC₂H₅ | |
| 5.17 | OC₂H₅ | OCH₃ | |
| 5.18 | SC₂H₅ | SCH₃ | |
| 5.19 | OC₂H₅ | OC₂H₅ | |
| 5.20 | SC₂H₅ | SC₂H₅ | |

TABLE 5-continued

Compound of the formula

| Compound | R_a | R_b | Physical data [°C.] |
|---|---|---|---|
| 5.21 | SC₂H₅ | OCH₂CH=CH₂ | |
| 5.22 | OC₂H₅ | SCH₃ | |
| 5.23 | OC₂H₅ | SC₂H₅ | |
| 5.24 | S(O)₂CH₃ | S(O)₂CH₃ | |
| 5.25 | SC₃H₇—i | SC₃H₇—i | |
| 5.26 | S(O)₂C₂H₅ | S(O)₂C₂H₅ | |
| 5.27 | OC₂H₅ | S(O)₂CH₃ | |
| 5.28 | S(O)₂C₃H₇—i | S(O)₂C₃H₇—i | |
| 5.29 | S(O)₂CH₃ | S(O)₂C₂H₅ | |
| 5.30 | S(O)CH₃ | S(O)CH₃ | |
| 5.31 | OC₂H₅ | S(O)₂C₂H₅ | |
| 5.32 | S(O)₂C₂H₅ | S(O)₂CH₃ | |
| 5.33 | OCH₂CH=CH₂ | SCH₃ | |
| 5.34 | OCH₂C≡CH | SCH₃ | |

TABLE 6

Compounds of the formula with R₁, R₂, R₃, R₄, R₅ substituents

| Compound | R₁ | R₂ | R₃ | R₄ | R₅ | Physical data [°C.] m.p. |
|---|---|---|---|---|---|---|
| 6.1 | NO₂ | CF₃ | Cl | CO—CH₃ | Cl | |
| 6.2 | CF₃ | NO₂ | H | CO—CH₃ | Cl | |
| 6.3 | NO₂ | CF₃ | Cl | CO—CH₂—Cl | Cl | |
| 6.4 | NO₂ | CF₃ | Cl | CO—CH₃ | OCH₃ | |
| 6.5 | CF₃ | NO₂ | H | CO—CH₂Cl | Cl | |
| 6.6 | NO₂ | CF₃ | Cl | CO—CH₃ | SCH₃ | 157–159 |
| 6.7 | NO₂ | CF₃ | Cl | CO—CH₂OCH₃ | Cl | |
| 6.8 | CF₃ | NO₂ | H | CO—CH₃ | SCH₃ | |
| 6.9 | CF₃ | NO₂ | H | CO—CH₂OCH₃ | Cl | |
| 6.10 | NO₂ | CF₃ | Cl | CO—CH₂OC₂H₅ | Cl | |
| 6.11 | NO₂ | CF₃ | Cl | CO—CH₂OCH₃ | SCH₃ | 98–102 |
| 6.12 | NO₂ | CF₃ | Cl | CO—CH₂Cl | SCH₃ | 45–49 |

TABLE 7

Compounds of the formula

F₃C, NO₂, NO₂ on benzene; NH to pyrimidine with Hal, R

| Compound | R | Hal | Physical data [°C.] |
|---|---|---|---|
| 7.1 | Cl | Cl | m.p. 213–214 |
| 7.2 | OCH₃ | F | resin |
| 7.3 | OC₃H₇—i | Cl | |
| 7.4 | S(O)₂CH₃ | Cl | |
| 7.5 | F | F | resin |
| 7.6 | OC₂H₅ | Cl | |
| 7.7 | OCH₃ | Cl | m.p. 212–214 |

TABLE 7-continued

Compounds of the formula

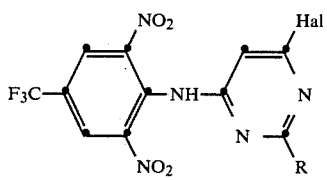

| Compound | R | Hal | Physical data [°C.] |
|---|---|---|---|
| 7.8 | $OC_2H_5$ | F | resin |
| 7.9 | $S(O)_2C_2H_5$ | Cl | |
| 7.10 | $OC_3H_7$—n | Cl | m.p. 122,5-123,5 |
| 7.11 | $S(O)CH_3$ | Cl | |
| 7.12 | Br | Br | resin |
| 7.13 | $OC_4H_9$—n | Cl | |
| 7.14 | S—cyclohexyl | Cl | |
| 7.15 | I | I | |
| 7.16 | $OC_3H_7$—i | F | |
| 7.17 | $OC_4H_9$—t | Cl | |
| 7.18 | $S(O)_2C_2H_5$ | Cl | |
| 7.19 | $SCH_3$ | F | |
| 7.20 | $S(O)_2C_3H_7$—n | Cl | |
| 7.21 | $OCH_2CH(CH_3)C_2H_5$ | Cl | |
| 7.22 | $OCH(CH_3)C_2H_5$ | Cl | semicristalline |
| 7.23 | $OC_5H_{11}$—n | Cl | |
| 7.24 | O—cyclohexyl | Cl | |
| 7.25 | $SC_2H_5$ | F | |
| 7.26 | $OC_6H_{11}$—n | Cl | |
| 7.27 | $OCH_3$ | Br | resin |
| 7.28 | $OC_6H_{13}$—n | F | |
| 7.29 | $SC_4H_9$—t | F | |
| 7.30 | $OC_2H_5$ | Br | resin |
| 7.31 | $OCH_2CH(CH_3)CH_2CH_2CH_3$ | Cl | |
| 7.32 | $SCH_3$ | Cl | m.p. 181-183 |
| 7.33 | $OC_3H_7$—i | Br | |
| 7.34 | $OCH_2CH(C_2H_5)_2$ | Cl | |
| 7.35 | $OCH_2CH_2OCH_3$ | F | |
| 7.36 | $SCH_3$ | Br | |
| 7.37 | $OC(CH_3)C\equiv CH$ | Cl | |
| 7.38 | $S(O)_2CH_3$ | F | |
| 7.39 | $SC_4H_9$—n | Cl | |
| 7.40 | $SC_2H_5$ | Cl | |
| 7.41 | $SCH_2CH=CH_2$ | Cl | |
| 7.42 | $OCH_2CF_3$ | Cl | semicristalline |
| 7.43 | $S(O)_2C_2H_5$ | F | |
| 7.44 | $SC_2H_5$ | Br | |
| 7.45 | $SC_3H_7$—n | Cl | |
| 7.46 | $SC_3H_7$—i | Br | |
| 7.47 | $SC_3H_7$—i | Cl | |
| 7.48 | $OC(CH_3)_2C\equiv CH$ | Cl | |
| 7.49 | $OCH_3C\equiv CH$ | Cl | semicristalline |
| 7.50 | $OCH_2CH_2Br$ | Br | |
| 7.51 | $S(O)_2CH_3$ | Br | |
| 7.52 | $S(O)_2C_6H_{13}$—n | F | |
| 7.53 | $SC_4H_9$—n | Cl | |
| 7.54 | $S(O)_2C_2H_5$ | Br | |
| 7.55 | $OCH_2CH=CH_2$ | Cl | semicristalline |
| 7.56 | $OCH_3$ | I | |
| 7.57 | $SC_4H_9$—t | Cl | |
| 7.58 | $OCH_2CH_2Br$ | Cl | resin |
| 7.59 | $OCH_2CH(CH_3)_2$ | Cl | m.p. 138-142 |
| 7.60 | $OCH_2CH_2OC_2H_5$ | Cl | |
| 7.61 | $OC_3H_7$—i | I | |
| 7.62 | $SCH_3$ | I | |
| 7.63 | $OCH_2CH_2Cl$ | Cl | |
| 7.64 | $S(O)_2CH_3$ | I | |
| 7.65 | $OCH_2CH=CH_2$ | $OCH_2CH=CH_2$ | oil |
| 7.66 | $OCH_2CH_2CH_2Cl$ | Cl | |
| 7.67 | $SC_2H_5$ | I | |
| 7.68 | $OCH_2CH=CH_2$ | I | |
| 7.69 | $OCH_2CH_2OCH_3$ | Cl | |
| 7.70 | $OCH_3$ | $OCH_3$ | m.p. 168-170 |

FORMULATION EXAMPLES

Formulation Examples for liquid active ingredients of the formula I (throughout, percentages are by weight)

| F1. Emulsifiable concentrates | (a) | (b) | (c) |
|---|---|---|---|
| a compound of tables 1 to 7 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| F2. Solutions | (a) | (b) | (c) | (d) |
|---|---|---|---|---|
| a compound of tables 1 to 7 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| F3. Granulates | (a) | (b) |
|---|---|---|
| a compound of tables 1 to 7 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| F4. Dusts | (a) | (b) |
|---|---|---|
| a compound of tables 1 to 7 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples for solid active ingredients of the formula I (throughout, percentages are by weight)

| F5. Wettable powders | (a) | (b) | (c) |
|---|---|---|---|
| a compound of tables 1 to 7 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| F6. Emulsifiable concentrate | |
|---|---|
| a compound of tables 1 to 7 | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| F7. Dusts | (a) | (b) |
|---|---|---|
| a compound of tables 1 to 7 | 5% | 8% |
| talcum | 95% | — |
| kaolin | — | 92% |

Ready-for-use dusts are obtained by mixing the active ingredient with the carriers, and grinding the mixture in a suitable mill.

| F8. Extruder granulate | |
|---|---|
| a compound of tables 1 to 7 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a strem of air.

| F9. Coated granulate | |
|---|---|
| a compound of tables 1 to 7 | 3% |
| polyethylene glycol 200 | 3% |
| kaolin | 94% |

The finely ground active ingredient is uniformly applied, in a mixer, to the kaolin moistened with polyethlene glycol. Non-dusty coated granulates are obtained in this manner.

| F10. Suspension concentrate | |
|---|---|
| a compound of tables 1 to 7 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the aduvants, giving a suspension concentrate from which suspensions of any desired concentration can be obtained by dilution with water.

BIOLOGICAL EXAMPLES

Example B1:

Action against Puccinia graminis on wheat (a) Residual-protective action Wheat plants are treated 6 days after sowing with a spray mixture prepared from a wettable powder formula ion of the active ingredient (0.02%). After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

(b) Systemic action

Wheat plants are treated 5 days after sowing with a spray mixture prepared from a wettable powder formulation of the active ingredient (0.006%) based on the volume of the soil). After 48 hours the treated plants are infected with a uredospore suspension of the fungus. The plants are then incubated for 48 hours at 95–100% relative humidity and about 20° C. and then stood in a greenhouse at about 22° C. Evaluation or rust pustule development is made 12 days after infection.

Compounds of Tables 1, 2 and 7, in particular compounds of groups Ib and Id, are very effective against Puccinia fungi. Puccinia attack on untreated and infected control plants was 100%. Compounds 1.1, 1.4, 1.5, 1.8, 2.1, 2.2, 2.5, 2.6, 2.7, 2.8, 2.12, 2.27, 2.32, 2.40, 2.42, 2.49, 7.2, 7.5, 7.32 and others inhibited Puccinia attack to 0 to 5%.

Example B2:

Action against Cercospora arachidicola in groundnut plants

Residual protective action

Groundnut plants 10–15 cm in height are sprayed with a spray mixture (0.006%) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected controls (number and size of the specks=100%), Cercospora attack on groundnut plants treated with compounds of groups Ib and Id is substantially reduced. In the above tests, compounds 1.1, 1.5, 1.8, 1.63, 1.80, 2.2, 2.3, 2.32, 2.40, 7.1 and 7.32 inhibited the occurrence of specks almost completely (0–10%).

Example B3:

Action against Erysiphe graminis on barley (a) Residual protective action

Barley plants about 8 cm in height are sprayed with a spray mixture (0.002%) prepared from the active ingredient formulated as a wettable powder. The treated plants are dusted with conidia of the fungus after 3–4 hours. The infected barley plants are then stood in a greenhouse at about 22° C. The extent of the infestation is evaluated after 10 days.

(b) Systemic action

Barley plants about 8 cm in height are treated with a spray mixture (0.002%), based on the volume of the soil) prepared from the test compound formulated as wettable powder. Care is taken that the spray mixture does not come in contact with the parts of the plants above the soil. The treated plants are infected 48 hours later with a conidia suspension of the fungus. The infected barley plants are then stood in a greenhouse at about 22° C. and evaluation of infestation is made after 10 days.

Compounds of formula I, in particular those of groups Ib and Id, are very effective against Erysiphe fungi. Erysiphe attack was 100% on untreated and iunfected control plants. Compounds of Tables 1 to 7, for example compounds 7.1, 7.5, 7.12 and others, inhibited fungus attack on barley to less than

Example B4:

Residual-protective action against Venturia inaequalis on apple shoots

Apple cuttings with 10–20 cm long fresh shoots are sprayed with a spray mixture (0.006%) prepared from a wettable powder formulation of the test compound. The plants are infected 24 hours later with a conidia suspension of the fungus. The plants are then incubated for 5 days at 90–100% relative humidity and stood in a greenhouse for a further 10 days at 20°–24° C. Scab infestation is evaluated 15 days after infection. Compounds of Tables 1 to 7, e.g. compounds 1.4, 1.5 and 1.12, inhibited attack to less than 25%. On the other hand, attack on untreated and infected control shoots was 100%.

Example B5:

Action against Botrytis cinerea on beans Residual protective action

Bean plants about 10 cm in height are sprayed with a spray mixture (0.02% concentration) prepared from a wettable powder formulation of the test compound. After 48 hours, the treated plants are infected with a conidia suspension of the fungus. The infected plants are incubated for 3 days at 95–100% relative humidity and 21° C., and evaluation of fungus attack is then made. Numerous compounds of Tables 1 to 7 very strongly inhibit the fungus infection. At a concentration of 0.02%, compounds of Tables 1, 2 and 7, e.g. compounds 1.1, 1.4, 1.5, 1.8, 1.12, 7.1 and 7.32, were fully effective (0 to 8% attack). Botrytis attack on untreated and infected bean plants was 100%.

Example B6:

Action against Phytophthora infestans on tomato plants (a) Residual protective action After a cultivation period of 3 weeks, tomato plants are sprayed with a spray mixture (0.06%) prepared from a wettable powder formulation of the test compound. After 24 hours the treated plants are infected with a sporangia suspension of the fungus. Evaluation of fungus attack is made is made after the plants have been incubated for 5 days at 90–100% relative humidity and 20° C.

(b) Systemic action

A spray mixture (0.06%, based on the volume of the soil) prepared from a wettable powder formulation of the test compound is poured on tomato plants after a cultivation period of 3 weeks. Care is taken that the spray mixture does not come in contact with the parts of the plants above the soil. After 48 hours the plants are infected with a sporangia suspension of the fungus. Evaluation of fungus attack is made after the plants have been incubated for 5 days at 90-100% relative humidity and 20° C.

In the above tests, compounds of the subgroups Ib and Id in particular have a very good systemic action, e.g. compounds 1.1, 1.2, 1.4, 1.5, 1.7, 1.8, 1.12, 1.16, 1.20, 1.37, 1.49, 1.57, 1.74, 1.80, 1.84, 2.1, 2.2, 2.5, 2.6, 2.7, 2.8, 2.27, 2.32, 2.49, 2.55, 4.4, 7.7 and 7.32. These compounds inhibited fungus attack almost completely (0 to 5% attack) as against 100% attack on untreated control plants.

EXAMPLE B7

Action against Plasmapora viticola on vines (a) Residual protective action

Vine cuttings in the 4-5 leaf stage are sprayed with a spray mixture (0.06%) prepared from a wettable powder formulation of the test compound. After 24 hours the treated plants are infected with a sporangia suspension of the fungus. Fungus attack is evaluated after incubation for 6 days at 95-100% relative humidity and 20° C.

(b) Residual curative action

Vine cuttings in the 4-5 leaf stage are infected with a sporangia suspension of the fungus. After incubation for 24 hours in a humid chamber at 95-100% relative humidity and 20° C., the infected plants are dried and sprayed with a spray mixture (0.06%) prepared from a wettable powder formulation of the test compound. After the spray coating has dried, the treated plants are returned to the humid chamber. Evaluation of fungus attack is made 6 days after infection.

Compounds of Tables 1, 2 and 7 have a very good fungicidal action against Plasmopara viticola on vines. In particular, compounds 1.1, 1.4, 1.5, 1.8 and 7.32 inhibited fungus attack completely (0 to 5%).

Example B8

Action against Piricularia on rice plants Residual protective action

After a cultivation period of 2 weeks, rice plants are sprayed with a spray mixture (0.02%) prepared from a wettable powder formulation of the test compound. After 48 hours the treated plants are infected with a conidia suspension of the fungus. Evaluation of fungus attack is made after incubation for 5 days at 95-100% relative humidity and 24° C.

Compared with 100% attack on untreated controls, fungus attack was less than 10% on rice plants which have been treated with one of compounds 1.1, 1.4, 1.5, 1.8 and 7.32.

What is claimed is:

1. A compound of the formula I

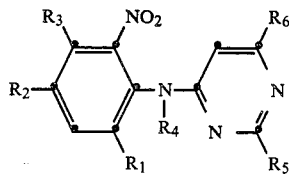

(I)

wherein
$R_1$ is $NO_2$ or $CF_3$,
$R_2$ is $NO_2$ or $CF_3$,
$R_3$ is hydrogen or halogen, $R_4$ is hydrogen or the —C(O)$R_7$ group, wherein $R_7$ is $C_1$-$C_4$alkyl which is unsubstituted or substituted by halogen, $C_1$-$C_3$alkoxy or $C_1$-$C_3$alkylthio, $R_5$ and $R_6$ are each independently halogen, $C_1$-$C_6$alkoxy, $C_1$-$C_6$alkyl which is substituted by halogen or $C_1$-$C_3$alkoxy, $C_1$-$C_6$alkoxy which is substituted by halogen or $C_1$-$C_3$alkoxy, $C_1$-$C_6$alkylthio or $C_1$-$C_6$alkylthio which is substituted by halogen or $C_1$-$C_3$alkoxy, or are $C_3$-$C_6$cycloalkoxy, $C_3$-$C_6$cycloalkylthio, $C_3$-$C_6$alkenyloxy, $C_3$-$C_6$alkenylthio, $C_3$-$C_6$alkynyloxy, $C_1$-$C_6$alkylsulfoxyl, $C_1$-$C_6$alkylsulfonyl, $C_1$-$C_6$alkylsulfonyloxy, $C_3$-$C_6$alkenylsulfoxyl, $C_3$-$C_6$alkenylsulfonyl, $C_3$-$C_6$cycloalkylsulfoxyl or $C_3$-$C_6$cycloalkylsulfonyl.

2. A compound of the formula I according to claim 1, wherein $R_1$ is $NO_2$, $R_2$ is $CF_3$, $R_3$ is chlorine and $R_4$ is hydrogen, $R_5$ is halogen, $C_1$-$C_6$alkoxy, chlorine- or bromine-substituted $C_1$-$C_3$alkyl, $C_1$-$C_3$-alkoxy-substituted $C_1$-$C_3$alkoxy, $C_1$-$C_6$alkylthio, cyclopentyloxy, cyclohexyloxy, cyclopentylthio, cyclohexylthio, $C_3$-$C_6$alkenyloxy, $C_3$-$C_6$alkenylthio, $C_3$-$C_6$alkynyloxy, $C_1$-$C_3$alkylsulfoxyl, $C_1$-$C_6$alkylsulfonyl, $C_1$-$C_3$alkylsulfonyloxy or cyclohexysulfonyl; and $R_6$ is halogen.

3. A compound of the formula I according to claim 1, wherein $R_1$ is $NO_2$, $R_2$ is $CF_3$, $R_3$ is chlorine or bromine, $R_5$ is halogen, $C_1$-$C_4$-alkoxy, $C_1$-$C_3$alkyl which is substituted by chlorine or bromine, $C_1$-$C_2$alkoxy which is substituted by methoxy, $C_1$-$C_4$alkylthio, $C_3$-$C_4$-alkenyloxy, $C_3$-$C_4$alkynyloxy or $C_1$-$C_3$alkylsulfonyl; and $R_6$ is fluorine, chlorine or bromine.

4. A compound of the formula I according to claim 1, wherein $R_1$ is $CF_3$, $R_2$ is $NO_2$, $R_3$ is hydrogen and $R_4$ is hydrogen, $R_5$ is halogen, $C_1$-$C_6$alkoxy, chlorine- or bromine-substituted $C_1$-$C_3$alkyl, $C_1$-$C_3$alkoxy-substituted $C_1$-$C_3$alkoxy, $C_1$-$C_6$alkylthio, cyclopentyloxy, cyclohexyloxy, cyclopentylthio, cyclohexylthio, $C_3$-$C_6$alkenyloxy, $C_3$-$C_6$alkenylthio, $C_3$-$C_6$alkynyloxy, $C_1$-$C_3$alkylsulfoxyl, $C_1$-$C_6$alkylsulfonyl, $C_1$-$C_3$alkylsulfonyloxy or cyclohexylfonyl; and $R_6$ is halogen.

5. A compound of the formula I according to claim 1, wherein $R_1$ is $CF_3$, $R_2$ is $NO_2$, $R_3$ is chlorine or bromine, $R_5$ is halogen, $C_1$-$C_4$alkoxy, chlorine- or bromine-substituted $C_1$-$C_3$alkyl, methoxy-substituted $C_1$-$C_2$alkoxy, $C_1$-$C_4$alkylthio, $C_3$-$C_4$alkenyloxy, $C_3$-$C_4$alkynyloxy, or $C_1$-$C_3$alkylsulfonyl; and $R_6$ is fluorine, chlorine or bromine.

6. A compound of the formula I according to claim 1, wherein $R_1$ is $NO_2$, $R_2$ is $CF_3$, $R_3$ is halogen and $R_4$ is hydrogen, $R_5$ is $C_1$-$C_3$-alkoxy, $C_1$-$C_3$alkylthio, $C_1$-$C_3$alkylsulfoxyl or $C_1$-$C_3$alkylsulfonyl; and $R_6$ is halogen.

7. A compound of the formula I according to claim 1, wherein $R_1$ is $NO_2$, $R_2$ is $CF_3$, $R_3$ is chlorine and $R_4$ is hydrogen, and each of $R_5$ and $R_6$ independently is halogen, $C_1$-$C_6$alkoxy, chlorine- or bromine-substituted $C_1$-$C_3$alkyl, $C_1$-$C_3$alkoxy-substituted $C_1$-$C_3$alkoxy, $C_1$-$C_6$alkylthio, cyclopentyloxy, cyclohexyloxy, cyclopentylthio, cyclohexylthio, $C_3$-$C_6$alkenyloxy, $C_3$alkenylthio, $C_3$-$C_6$alkynyloxy, $C_1$-$C_3$-alkylsulfoxy, $C_1$-$C_6$alkylsulfonyl, $C_1$-$C_3$alkylsulfonyloxy or cyclohexylsulfonyl.

8. A compound of the formula I according to claim 1, wherein $R_1$ is $CF_3$, $R_2$ is $NO_2$, $R_3$ is hydrogen and $R_4$ is hydrogen, and each of $R_5$ and $R_6$ independently is $C_1$-$C_3$alkoxy, $C_1$-$C_3$alkylthio, $C_3$alkenyloxy, $C_1$-$C_3$alkenylsulfoxyl or $C_1$-$C_3$alkenylsulfonyl.

9. A compound of the formula I according to claim 1, wherein $R_1$ is $CF_3$ or $NO_2$, $R_2$ is $CF_3$ or $NO_2$, $R_3$ is hydrogen or chlorine, $R_4$ is the C(O)—$R_7$ group, wherein $R_7$ is $C_1-C_3$alkyl, halogen-substituted $C_1-C_3$alkyl or $C_1-C_3$alkoxy-substituted $C_1-C_3$alkyl; $R_5$ is halogen, $C_1-C_3$alkoxy or $C_1-C_3$alkylthio, and $R_6$ is chlorine, $C_1-C_3$alkylthio and $R_6$ is chlorine.

10. A compound of the formula I according to claim 1, wherein $R_1$ is $NO_2$, $R_2$ is $CF_3$, $R_3$ is hydrogen and $R_4$ is hydrogen, $R_5$ is halogen, $C_1-C_6$alkoxy, chlorine- or bromine-substituted $C_1-C_3$alkyl, $C_1-C_3$-alkoxy-substituted $C_1-C_3$alkoxy, $C-C_6$alkylthio, cyclopentyloxy, cyclohexyloxy, cyclopentylthio, cyclohexylthio, $C_3-C_6$alkenyloxy, $C_3-C_6$alkenylthio, $C_3-C_6$alkynyloxy, $C_1-C_3$alkylsulfoxy, $C_1-C_6$alkylsulfonyl, $C_1-C_3$alkylsulfonyloxy or cyclohexylsulfonyl; and $R_6$ is halogen.

11. A compound according to claim 1 wherein:
R1 is NO2 or CF3,
R2 is NO2 or CF3,
R3 is hydrogen, fluorine, chlorine or bromine,
R4 is hydrogen, and
R5 and R6 are each independently halogen, C1–C4-alkoxy, C1–C4-haloalkoxy or C1–C4-alkylthio.

12. A compound of the formula I according to claim 11, selected from the group consisting of
N-(3'-chloro-2',6'-dinitro-4'-trifluoromethylphenyl)-4-amino-2,6-dichloropyrimidine;
N-(2',4'-dinitro-6'-trifluoromethylphenyl)-4-amino-2,6-dichloropyrimidine;
N-(3'-chloro-2',6'-dinitro-4'-trifluoromethylphenyl)-4-amino-6-chloro-2-methylthiopyrimidine,
N-(2',6'-dinitro-4'-trifluoromethylphenyl)-4-amino-6-chloro-2-methylthiopyrimidine;
N-(3'-chloro-2',6'-dinitro-4'-trifluoromethylphenyl)-4-amino-6-chloro-2-methoxypyrimidine;
N-(3'-chloro-2',6'-dinitro-4'-trifluoromethylphenyl)-4-amino-6-chloro-2-ethoxypyrimidine;
N-(3'-chloro-2',6'-dinitro-4'-trifluoromethylphenyl)-4-amino-6-chloro-2-ethylthiopyrimidine;
N-(3'-chloro-2',6'-dinitro-4'-trifluoromethylphenyl)-4-amino-6-chloro-2-sec-butylthiopyrimidine;
N-(2',6'-dinitro-4'-trifluoromethylphenyl)-4-amino-2,6-dichloropyrimidine;
N-(2',4'-dinitro-6'-trifluoromethylphenyl)-4-amino-2-methoxy-6-chloropyrimidine;
N-(2',4'-dinitro-6'-trifluoromethylphenyl)-4-amino-2-ethoxy-6-chloropyrimidine.

13. A composition for controlling or preventing attack by micro-organisms, which contains at least one compound according to claim 1.

14. A composition according to claim 13, which contains at least one compound according to claim 2.

15. A composition according to claim 13, which contains at least one compound according to claim 3.

16. A method of controlling phytopathogenic micro-organisms or of preventing cultivated plants from being attacked by such micro-organisms, which comprises applying to said plants or to the locus thereof an effective amount of a compound of the formula I as defined in claim 1.

* * * * *